United States Patent [19]

Kook et al.

[11] Patent Number: 4,603,016
[45] Date of Patent: Jul. 29, 1986

[54] CRYOGENIC BRINE SEPARATION OF WATER AND ISOCYANATES

[75] Inventors: John F. Kook, Hockessin; John R. Kosak, Greenville, both of Del.

[73] Assignee: E. I. Du Pont de Nemours and Company, Wilmington, Del.

[21] Appl. No.: 798,117

[22] Filed: Nov. 14, 1985

[51] Int. Cl.$^4$ .............................................. C07C 71/00
[52] U.S. Cl. .................................... 560/352; 560/338
[58] Field of Search ................. 260/453 SP, 453 AL, 260/453 P

[56] References Cited

U.S. PATENT DOCUMENTS 4,207,251 6/1980 Heyboer .......................... 260/453 P

FOREIGN PATENT DOCUMENTS 4318534 1/1966 Japan ............................. 260/453 SP

*Primary Examiner*—Alan Siegel
*Attorney, Agent, or Firm*—Scott G. Hallquist

[57] ABSTRACT

Isocyanates produced by vapor-phase catalytic oxidative dehydrogenation of corresponding N-substituted formamides are readily separated from by-product water by contacting the reaction mixture, in the vapor phase, with a cold brine mixture comprising water and about 25% to about 35% by weight of a salt or salts selected from the group consisting of NaCl, CaCl$_2$, and MgCl$_2$, the brine mixture having been maintained at a temperature between about 0° C. and its freezing point prior to contact with the reaction mixture containing isocyanates.

19 Claims, No Drawings

4,603,016

CRYOGENIC BRINE SEPARATION OF WATER AND ISOCYANATES

BACKGROUND OF THE INVENTION

1. Technical Field

The present invention relates generally to processes for catalytic conversion of formamides and oxygen to isocyanates.

2. Description of the Prior Art

Heyboer, U.S. Pat. No. 4,207,251, discloses a method for gas phase production of $C_{1-24}$ organo-isocyanates involving oxidative dehydrogenation of corresponding N-monosubstituted formamides. The product stream obtained contains isocyanate, water, nitrogen or other inert gas, unreacted formamide, and residual by-products. This reference discloses several methods for separation of product isocyanates from water, which are summarized below.

A first method involves rapid cooling. Upon termination of the oxidative dehydrogenation reaction, the reaction mixture can be rapidly cooled, whereupon the water-containing phase and isocyanate-containing phase are separated by filtration or extraction. As noted by the Heyboer patent, disadvantages of this method include the high cost of rapid cooling, and the risk of reaction of water and isocyanate where cooling is insufficient and separation is not accomplished sufficiently rapidly.

A second method requires contacting the reaction mixture with a water-absorbing agent prior to condensation of isocyanate. Suitable agents include molecular sieves, for example, zeolite 3Å, or magnesium sulfate, sodium sulfate, and/or calcium chloride.

A third method involves condensation of product isocyanate in the presence of a substantially water-immiscible solvent, optionally in the presence of water absorbing agents. However, such "solvent-borne" isocyanate recovery processes require an additional partial condensation step to separate isocyanate from the recovery solvent, adding to overall process complexity and cost.

The present invention provides an improved method for separating water from isocyanate and water-containing process streams resulting from gas-phase oxidative dehydrogenation of formamides. The present invention offers an efficient, economic product recovery process providing high product recovery yields and ready adaptability to continuous operation. The process of the present invention is particularly suited for use in production of alkyl isocyanates such as methyl isocyanate.

SUMMARY OF THE INVENTION

The present invention provides a process for isolating isocyanates from a reaction mixture containing isocyanates produced by vapor-phase catalytic oxidative dehydrogenation of corresponding N-substituted formamides, the process comprising (a) contacting the reaction mixture, in the vapor phase, with a cold brine mixture, thereby providing isocyanate-containing and aqueous phases, and (b) separating the isocyanate-containing phase from the aqueous phase;

the process characterized by use of a brine mixture comprising water and about 25% to about 35% by weight of a salt or salts selected from the group consisting of NaCl, $CaCl_2$, and $MgCl_2$, which mixture is maintained at a temperature between 0° C. and its freezing point, prior to contact with the reaction mixture containing isocyanates.

DETAILED DESCRIPTION OF THE INVENTION

The present invention provides an improved process for isolating isocyanates produced by catalytic conversion of formamides in the presence of oxygen. Heyboer, U.S. Pat. No. 4,207,251, discloses a process for gas phase oxidation of N-monosubstituted formamides, wherein oxygen or an oxygen-containing gas such as air is added to the formamide and the resulting mixture passed over a copper and/or noble metal catalyst at a temperature from about 300° C. to 600° C. The catalysts employed can be copper and/or one or more metals selected from the group consisting of Ag, Au, Ru, Rh, Pd, Os, Ir, and Pt. Additional process details, such a reactants and process conditions, can be found in U.S. Pat. No. 4,207,251, the disclosure of which is incorporated herein by reference.

As used herein, the term "isocyanates" refers to compounds of the formula $R-(NCO)_n$, wherein R is a $C_{1-10}$ alkyl, cycloalkyl, aryl, alkaryl, or aralkyl group and n is 1 or 2, which are produced by catalytic oxidative dehydrogenation of a corresponding formamide of the formula $R(NH-CO-H)_n$.

Generally, in commercial processes for production of alkyl isocyanates, reactant N-monosubstituted formamides are vaporized, mixed with an inert gas such as nitrogen to provide process temperature control, and then mixed with oxygen or air in approximately stoichiometric amounts prior to introduction to a reactor in the gas phase at a temperature from about 250° C. to about 350° C.

As previously noted, the reaction is conducted in the presence of an active catalyst. Silver catalysts are preferred, or combinations of silver and one or more of the other metals disclosed in U.S. Pat. No. 4,201,251. Gold is preferably employed where the catalyst employed is silver in combination with another metal.

Oxidative dehydrogenation of formamides evolves a considerable amount of heat; within the reactor, process temperatures are maintained from about 400° C. to about 700° C., preferably from about 450° C. to about 650° C. Reaction temperatures greater than about 700° C. should be avoided to minimize the occurrence of yield-reducing side reactions and product decomposition. Reaction temperatures from about 500° C. to about 600° C. are particularly preferred. Reaction temperatures can be controlled by interstage cooling, addition of inert gas, decreasing the amount of oxygen or air added, or increasing reactant flow rates.

Immediately following contact with catalyst and formation of isocyanate, the reaction mixture contains by-products water and $CO_2$, unreacted formamide, isocyanate, and certain other by-products or impurities. In accordance with the present invention, the reaction mixture exiting the dehydrogenation reactor, while in the vapor phase, is contacted with a cold, dense brine comprising from about 25% to about 35% by weight of a salt or salts selected from the group consisting of NaCl, $CaCl_2$, and $MgCl_2$. A preferred salt for use in the process of the present invention is $CaCl_2$. Preferably, the brine comprises from about 29% to about 32% by weight, and most preferably, from about 30% to about 31% by weight $CaCl_2$. At this concentration of $CaCl_2$, the brine will exhibit a specific gravity from about 1.30 to about 1.35. Commercial grade $CaCl_2$, having a purity of about 98% by weight, can be employed.

The brine can be maintained at a temperature below 0° C. by recycling through a cryogenically cooled reservoir. Brine temperatures of from about −20° C. to about −40° C. are preferred, and temperatures from about −30° C. to about −35° C. are particularly preferred. These temperatures are determined by measuring the temperature of the brine stream prior to contact with the isocyanate-containing reaction mixture.

Following contact of the reactor effluent stream with the brine stream, which can occur, for example, in a vertical condenser, water is condensed from the effluent stream and is removed with the brine stream. Preferably, the condenser is configured to provide countercurrent flow of reactor effluent and brine streams. The isocyanate-containing phase can then be drawn from the condenser by conventional means. The brine or aqueous phase can be recycled through a refrigerated reservoir for subsequent reuse. Filtration of the brine stream to remove solid $CaCO_3$ or other by-products can optionally be incorporated into the recycling process. Additional $CaCl_2$ or other salt should be added periodically to the reservoir to maintain brine composition within acceptable limits. Excess salt solution should be purged from the system on a periodic basis.

The resulting separated isocyanate phase can then be further dried by contact with a molecular sieve, for example zeolite 3 Å, prior to further purification and/or consumption in a subsequent process. As noted below, the isocyanate-containing phase produced by the separation method of the present invention will typically contain from 90–98% isocyanate.

The most preferred application of the present process is in production of methyl isocyanate from monomethylformamide. Methyl isocyanate is employed in the production of certain insecticides, particularly S-methyl-N-[(methylcarbamoyl)oxyl]thioacetimidate (methomyl).

EXAMPLES

The following examples illustrate particular aspects of the present invention. In the examples, all degrees are reported in degrees Celsius (°C.) and all percentages are by weight unless otherwise indicated.

EXAMPLE 1

Liquid monomethylformamide (MMF) was fed to a preheater at a rate of 1.0 mL/min, continuously vaporized and preheated to about 240°. The resulting preheated MMF vapor was then fed to a reactor at a rate of 380 mL/minute, together with 542 mL/min air fed through the preheater, and 363 mL/min air added prior to introduction to the reactor. Thus, the relative percentage composition, by weight, of the gas mixture flowing to the reactor was as follows: $N_2$—58.0; $O_2$—14.5; MMF—27.5. This provided a molar ratio of oxygen to MMF which was approximately 1.0. Flow rates were measured using a mass flow meter.

The reactor employed was a quartz U-tube reactor (10 mm inside diameter; 60 cm length) containing 8 g of crystalline silver catalyst, at a catalyst bed depth of 2.5 cm. The reaction tube was equipped with a thermocouple to measure the temperature of the catalyst bed, and the reactor was immersed in a sand bed maintained at 450°. The sand bed was equipped with an electric heater to initially elevate the temperature of the catalyst bed to about 530°, representing a level sufficient to start the reaction.

The effluent from the reactor was initially monitored by gas chromatography (GC) to verify reaction progress. At this point, the effluent from the reactor was routed to a tube condenser through which a 30.5% $CaCl_2$ solution, cooled to about −30° by contact with a dry ice bath, was flowing. The condenser was connected to a decanter having an upper outlet leading to a −40° cold trap, and a lower outlet through which brine was routed back to a dry-ice cooled reservoir. A pump was employed to circulate brine through the condenser at a rate of about 450 mL/min. The condenser was vented through a vessel containing monomethylamine, to trap unreacted MMF and methyl isocyanate (MIC) which had not been collected by the condenser/decanter apparatus. The condenser head was fitted with a thermometer to measure exiting gas temperature at the top of the condenser. This thermometer indicated a minimum temperature of 22° during this experiment.

This arrangement was allowed to run for about 30 min. at the feed rates indicated above (about 1 mole MMF/hr) and then the reactant feed rates were increased to provide about 2 moles MMF/hr. 70.9 g of organic material were isolated in the cold trap; GC analysis indicated 96.5% MIC. Based upon a total MMF feed of 90 g, the organic fraction recovered in the cold trap represented an MIC yield of 78.7%.

EXAMPLE 2

Example 1 was substantially repeated, except that the molar ratio of oxygen to MMF fed to the reactor was increased to 1.05. Liquid MMF was fed to the system at 2.0 mL/min. After 1.5 hr, a product fraction weighing 107.1 g and containing 97% MIC was isolated from the cold trap, representing a total MIC recovery of 62%. A significant amount of gaseous effluent was observed exiting from the vent at the top of the brine condenser, probably representing a loss of product MIC.

At this point, all reactant flows were halved and the system was operated for an additional 1.5 hr. A product fraction weighing 61.2 g, containing 97.5% MIC, was isolated from the cold trap, representing a 70% recovery. The temperature at the top of the condenser head during this experiment remained at approximately 17°.

EXAMPLE 3

This example illustrates use and recycling of a brine solution prepared from commercial-grade $CaCl_2$. Example 1 was substantially repeated, except that a 30.5% $CaCl_2$ solution was prepared using commercial-grade (98% purity) $CaCl_2$. 2 mL/min liquid MMF was fed to the preheater, resulting in a flow of MMF vapor of 760 mL/min to the reactor. A total of 1870 mL/min air was also fed to the reactor. During this experiment, the catalyst bed temperature was maintained at 610°. Following equilibration, MIC was trapped using the brine condenser. During the first hour of operation, 70.8 g MIC were recovered, representing a yield of 62%. During the second hour of operation, 78.7 g MIC were recovered by the brine condenser, representing a yield of 69%.

On the following day, the reactor and brine condenser apparatus were restarted and operated at the same feed rates described in the preceding paragraph. However, prior to use, the brine solution was adjusted to a specific gravity of 1.3 by addition of $CaCl_2$, and filtered to remove solid $CaCO_3$. The apparatus was run for three hours. During the first hour, 66.7 g MIC were recovered; during the second hour of operation, 78.2 g were recovered; and during the third hour, 86.8 g.

2000 g CaCl$_2$ brine were recovered for reuse. Filtration removed 10.4 g CaCO$_3$. 150 g CaCl$_2$ were added to raise the specific gravity of the brine to 1.35. This recovered brine was reused on the following day in the MIC reactor/brine condenser apparatus, which was operated at the same feed rates previously described. Samples were again collected for one hour periods from the brine condenser. The following table indicates the weight and composition (as determined by GC analysis) of the samples collected during a three hour period following equilibration of the apparatus. In addition, a sample of the condenser brine and of a solid residue collected in the MMA vent trap were analyzed. In Table 1, below, DMU refers to dimethylurea; TMB refers to N, N', N''-trimethylbiuret; and "Trimer" refers to 1,3,5-trimethyl-1,3,5-triazine-2,4,6(1H, 3H, 5H)-trione.

TABLE 1

| Sample | Component Analysis (GC Area Percent) | | | | |
|---|---|---|---|---|---|
| | MIC | MMF | DMU | TMB | Trimer |
| 1st hr | 97.1 | 0.34 | 0.57 | 0.55 | — |
| 2nd hr | 96.5 | 0.41 | 0.68 | 0.61 | — |
| 3rd hr | 96.9 | 0.37 | 0.54 | 0.45 | — |
| Brine | — | 2.70 | 0.97 | ND | ND |
| MMA Trap | — | 17.6 | 83.4 | ND | ND |

ND = not determined.

EXAMPLE 4

This example illustrates the stability of MIC preparations isolated by the process of the present invention. The procedure described in Example 1 was substantially repeated at MMF liquid feed rates of 2 mL/min. As described in Example 3, samples of the product of the brine condenser were collected for one hour periods, weighed, and yields estimated. Each sample was then analyzed by GC to determine MIC content immediately following collection, and again after storage for two weeks. The results of these determinations, which are set forth in Table 2, below, indicate minimal degradation of product MIC during storage.

TABLE 2

| Sample | Weight Yield | | % MIC | |
|---|---|---|---|---|
| | (g) | (%) | As Isolated | After Storage |
| 1st hr | 79.7 | 69 | >98 | 92.3 |
| 2nd hr | 69.3 | 60 | >98 | 92.3 |
| 3rd hr | 99.2 | 86 | >98 | 93.1 |
| 4th hr | 80.5 | 70 | >98 | 95.0 |
| 5th hr | 86.3 | 75 | >98 | 95.4 |

What is claimed is:

1. A process for isolating isocyanates from a reaction mixture containing isocyanates produced by vapor-phase catalytic oxidative dehydrogenation of corresponding N-substituted formamides, the process comprising
    (a) contacting the reaction mixture, in the vapor phase, with a cold brine mixture, thereby providing isocyanate-containing and aqueous phases, and
    (b) separating the isocyanate-containing phase from the aqueous phase;
    the process characterized by use of a brine mixture comprising water and about 25% to about 35% by weight of a salt or salts selected from the group consisting of NaCl, CaCl$_2$, and MgCl$_2$, which brine mixture is maintained at a temperature between 0° C. and its freezing point, prior to contact with the reaction mixture containing isocyanates.

2. A process according to claim 1, wherein the cold brine is continuously recycled for reuse.

3. A process according to claim 2, wherein the brine mixture is maintained at a temperature from about −40° C. to about −20° C. prior to contact with the reaction mixture containing isocyanates.

4. A process according to claim 3, wherein the brine mixture comprises from about 25% to about 35% by weight CaCl$_2$.

5. A process acccording to claim 3, wherein the brine comprises from about 29% to about 32% by weight CaCl$_2$.

6. A process according to claim 5, wherein the brine is maintained at a temperature from about −30° C. to about −35° C. prior to contact with the reaction mixture containing isocyanates.

7. A process according to claim 6, wherein the brine comprises from about 30% to about 31% by weight CaCl$_2$.

8. A process according to claim 1, wherein the isocyanates are alkyl isocyanates.

9. A process according to claim 8, wherein the isocyanate is methyl isocyanate.

10. A process according to claim 3, wherein the isocyanates are alkyl isocyanates.

11. A process according to claim 10, wherein the isocyanate is methyl isocyanate.

12. A process according to claim 4, wherein the isocyanates are alkyl isocyanates.

13. A process according to claim 12, wherein the isocyanate is methyl isocyanate.

14. A process according to claim 5, wherein the isocyanates are alkyl isocyanates.

15. A process according to claim 14, wherein the isocyanate is methyl isocyanate.

16. A process according to claim 6, wherein the isocyanates are alkyl isocyanates.

17. A process according to claim 16, wherein the isocyanate is methyl isocyanate.

18. A process according to claim 7, wherein the isocyanates are alkyl isocyanates.

19. A process according to claim 18, wherein the isocyanate is methyl isocyanate.

* * * * *